United States Patent
Honda et al.

(10) Patent No.: US 11,752,223 B2
(45) Date of Patent: Sep. 12, 2023

(54) METHOD FOR PRODUCING AC-225 SOLUTION AND METHOD FOR PRODUCING MEDICINE USING AC-225 SOLUTION

(71) Applicants: NIHON MEDI-PHYSICS CO., LTD., Tokyo (JP); NATIONAL INSTITUTES FOR QUANTUM SCIENCE AND TECHNOLOGY, Chiba (JP)

(72) Inventors: Yoshio Honda, Tokyo (JP); Taku Ito, Tokyo (JP); Jun Ichinose, Tokyo (JP); Hiroaki Ichikawa, Tokyo (JP); Tomoyuki Imai, Tokyo (JP); Kotaro Nagatsu, Chiba (JP); Hisashi Suzuki, Chiba (JP)

(73) Assignees: NIHON MEDI-PHYSICS CO., LTD., Tokyo (JP); NATIONAL INSTITUTES FOR QUANTUM SCIENCE AND TECHNOLOGY, Chiba (JP)

(*) Notice: Subject to any disclaimer, the term of this patent is extended or adjusted under 35 U.S.C. 154(b) by 0 days.

(21) Appl. No.: 17/869,104

(22) Filed: Jul. 20, 2022

(65) Prior Publication Data

US 2022/0370651 A1 Nov. 24, 2022

Related U.S. Application Data

(63) Continuation of application No. PCT/JP2022/000116, filed on Jan. 5, 2022.

(30) Foreign Application Priority Data

Jan. 8, 2021 (JP) .................. 2021-002437

(51) Int. Cl.
*A61K 51/08* (2006.01)
*A61K 51/04* (2006.01)

(52) U.S. Cl.
CPC ........ *A61K 51/088* (2013.01); *A61K 51/0497* (2013.01)

(58) Field of Classification Search
CPC .......................... A61K 51/088; A61K 51/0497
USPC ....................................................... 424/1.69
See application file for complete search history.

(56) References Cited

U.S. PATENT DOCUMENTS

2009/0191122 A1* 7/2009 Moreno Bermudez ......................
B01D 15/206
424/1.61

FOREIGN PATENT DOCUMENTS

| JP | H07203974 A | 8/1995 |
|---|---|---|
| JP | H115749 A | 1/1999 |
| JP | 2007508531 A | 4/2007 |
| JP | 2009527731 A | 7/2009 |
| JP | 2010502965 A | 1/2010 |
| JP | 2017538780 A | 12/2017 |
| WO | 02067999 A2 | 9/2002 |
| WO | 02067999 A3 | 10/2002 |
| WO | 2013157102 A1 | 10/2013 |
| WO | 2013157105 A1 | 10/2013 |
| WO | 2016186206 A1 | 11/2016 |
| WO | 2017217347 A1 | 12/2017 |
| WO | 2020256066 A1 | 12/2020 |
| WO | 2021002275 A1 | 1/2021 |
| WO | 2021033530 A1 | 2/2021 |
| WO | 2021075546 A1 | 4/2021 |

OTHER PUBLICATIONS

Kuznetsova et al. Radiochem. 2012, 54, 383-387. (Year: 2012).*
Engle et al. Radiochim. Acta 2014, 102, 569-581. (Year: 2014).*
International Search Report (PCT/ISA/210) with English translation, and Written Opinion KPCT/ISA/237) dated Feb. 22, 2022, by the Japan Patent Office as the International Searching Authority for International Application No. PCT/JP2022/000116. (10 pages).
Office Action dated Jul. 13, 2022, by the Korean Patent Office in corresponding Korean Patent Application No. 10-2022-7021372 with a machine English translation of the Office Action. (8 pages).
Apostolidis C, et al., "Cyclotron production of Ac-225 for targeted alpha therapy", Appl Radiat Isot, 2005, 62, pp. 383-387. (5 pages).
Bernhard et al., "DOTAGA-Anhydride: A Valuable Building Block for the Preparation of DOTA-Like Chelating Agents", Chem. Eur. J., 2012, 18, 25, pp. 7834-7841. (8 pages).
Inui, et al., "Radioimmunotherapy for Pancreatic Carcinoma Using 131I-Labeled Monoclonal Antibody Nd2 in Xenografted Nude Mice", Japanese Journal of Cancer Research, 1996, 87, pp. 977-984. (8 pages).
TALYS-based evaluated nuclear data library (TENDL-2019), website <https://tendl.web.psi.ch/tendl_2019/proton_html/Ra/ProtonRa226xs.html>, Accessed Jul. 19, 2022. (1 page).
Wang H et al., "Selective in vivo metabolic cell-labeling-mediated cancer targeting", Nat Chem Biol, 2017, 13, 4, pp. 415-424. (13 pages).
Notice of Allowance (Decision to Grant) dated Nov. 25, 2022, by the Korean Intellectual Property Office in corresponding Korean Patent Application No. 10-2022-7021372 and an English translation of the Notice (6 pages).

* cited by examiner

*Primary Examiner* — Michael G. Hartley
*Assistant Examiner* — Sean R Donohue
(74) *Attorney, Agent, or Firm* — BUCHANAN INGERSOLL & ROONEY PC (57) ABSTRACT

A method for producing an $^{225}$Ac solution includes a step (I) of irradiating a $^{226}$Ra target with particles to generate two or more actinium radioisotopes (Ac) including at least $^{225}$Ac, a step (II) of dissolving the $^{226}$Ra target after the aforementioned step to obtain a solution (1), a step (III) of separating $^{226}$Ra and Ac contained in the solution (1) to obtain a solution (2), a step (IV) of allowing Ac contained in the solution (2) other than $^{225}$Ac to decay to obtain a solution (3), and a step (V) of separating Ra and Ac contained in the solution (3) to obtain a solution (4). The solution (4) is used to produce a medicine that contains, as an active ingredient, a conjugate between a chelating agent that has formed a complex with $^{225}$Ac, and a targeting agent.

5 Claims, 3 Drawing Sheets

METHOD FOR PRODUCING AC-225 SOLUTION AND METHOD FOR PRODUCING MEDICINE USING AC-225 SOLUTION

TECHNICAL FIELD

An aspect of the present invention relates to a method for producing an $^{225}$Ac solution or a method for producing a medicine using the solution.

BACKGROUND ART

In the field of nuclear medicine, radionuclide therapy has been performed in which a radioisotope (RI)-containing drug is selectively incorporated to a lesion such as a tumor. Among radiation particles, an alpha-particles has a short range and thus unnecessary radiation exposure to the surrounding healthy cells have limited effects. $^{225}$Ac is one of alpha-particles-emitting nuclides, and is a radionuclide that has a half-life of 10 days. $^{225}$Ac has recently emerged as a promising therapeutic nuclide in cancer treatment, for example.

$^{225}$Ac is, for example, produced as a result of a (p, 2n) nuclear reaction by irradiating a $^{226}$Ra target with particles such as protons using an accelerator. JPA 2010-502965 discloses a method that involves separating and purifying the $^{225}$Ac component from a solution obtained by dissolving a $^{226}$Ra target after particle irradiation and containing $^{226}$Ra ions and $^{225}$Ac ions.

SUMMARY OF INVENTION

Radioisotopes of actinium obtained simultaneously with generation of $^{225}$Ac are, for example, $^{224}$Ac (half-life: 2.8 hours) and $^{226}$Ac (half-life: 29 hours). Since $^{224}$Ac and $^{226}$Ac have shorter half-lives than $^{225}$Ac, a predetermined resting period has been set to allow $^{224}$Ac and $^{226}$Ac to decay to nuclides of metals other than actinium, and then $^{225}$Ac and $^{226}$Ra have been separated. However, the inventors of the present invention have noticed that this method does not consider the products generated by nuclear fission of $^{226}$Ra.

During generation of $^{225}$Ac, $^{140}$Ba is generated by nuclear fission of $^{226}$Ra. Since $^{140}$Ba decays to $^{140}$La in a half-life of 12.75 days, providing a period for allowing $^{224}$Ac and $^{226}$Ac to decay generates $^{140}$La. $^{140}$La and $^{225}$Ac behave similarly and are thus difficult to separate, and this has posed some concern from the viewpoint of quality.

$^{140}$La has a half-life of 1.7 days and can be eliminated by decay; however, in the co-presence of $^{140}$Ba, the half-life of $^{140}$La becomes the same as the half-life of $^{140}$Ba due to radiation equilibrium, and thus, eventually, a rest period longer than the decay period of $^{224}$Ac and $^{226}$Ac is necessary if $^{140}$La is to be eliminated by decay, and this has posed a problem of loss of $^{225}$Ac.

An aspect of the present invention provides a method for producing an $^{225}$Ac solution having a high $^{225}$Ac concentration while reducing loss caused by radio-active decay of $^{225}$Ac.

The inventors of the present invention have conducted extensive studies to address the issues described above and found that the issues can be addressed by the following exemplary structures, and thus arrived at the present invention.

According to one aspect of the present invention, there is provided a method for producing an $^{225}$Ac solution, the method including:

a step (I) of irradiating a $^{226}$Ra target with at least one type of particles selected from protons, deuterons, neutrons, and photons to generate two or more actinium radioisotopes (Ac) including at least $^{225}$Ac;

a step (II) of dissolving the $^{226}$Ra target after the step (I) to obtain a Ra—Ac solution (1) that contains $^{226}$Ra and Ac;

a step (III) of separating $^{226}$Ra and Ac originating from the $^{226}$Ra target and contained in the Ra—Ac solution (1) to obtain an Ac solution (2) that has a higher Ac concentration (in particular, purity) than the Ra—Ac solution (1);

a step (IV) of allowing the actinium radioisotopes contained in the Ac solution (2) other than $^{225}$Ac to decay to obtain a Ra—Ac solution (3) containing radium isotopes (Ra) resulting from decay; and a step (V) of separating Ra and Ac contained in the Ra—Ac solution (3) to obtain an Ac solution (4) that has a higher $^{225}$Ac concentration (in particular, purity) than the Ra—Ac solution (3), in which the Ac solution (4) is used for producing a medicine indicated in (a) or (b) below:

(a) a medicine that contains, as an active ingredient, a conjugate between a chelating agent that has formed a complex with $^{225}$Ac, and an Nd2 antibody (b) a medicine that contains, as an active ingredient, a conjugate between a chelating agent that has formed a complex with $^{225}$Ac, and a targeting agent (excluding the Nd2 antibody).

According to another aspect of the present invention, there is provided a method for producing the above-described medicine, the method including a step (VIa) of allowing the chelating agent to form a complex with $^{225}$Ac by using an $^{225}$Ac solution obtained by performing the steps (I) to (V) described above.

According to an aspect of the present invention, an $^{225}$Ac solution having a high $^{225}$Ac concentration (in particular, purity) can be produced while suppressing the loss caused by radio-active decay of $^{225}$Ac.

BRIEF DESCRIPTION OF DRAWINGS

FIG. 2 shows gamma spectra of various $^{225}$Ac samples. (a) in FIG. 2 is a gamma spectrum of the $^{225}$Ac product (initial separation) four days after end of bombardment (EOB) in Example 2, (b) in FIG. 2 is a gamma spectrum of the $^{225}$Ac product (secondary separation) 20 days after EOB in Example 2, and (c) in FIG. 2 is a gamma spectrum of a commercially available reference $^{225}$Ac (generator-produced).

DESCRIPTION OF EMBODIMENTS

[Method for Producing $^{225}$Ac Solution]

A method for producing an $^{225}$Ac solution according to an embodiment of the present invention (hereinafter this method may also be referred to as the "present production method") includes: a step (I) of irradiating a $^{226}$Ra target with at least one type of particles selected from protons, deuterons, neutrons, and photons to generate two or more actinium radioisotopes (Ac) including at least $^{225}$Ac;

a step (II) of dissolving the $^{226}$Ra target after the step (I) to obtain a Ra—Ac solution (1) that contains $^{226}$Ra and Ac;

a step (III) of separating $^{226}$Ra and Ac originating from the $^{226}$Ra target and contained in the Ra—Ac solution (1) to obtain an Ac solution (2) that has a higher Ac concentration (in particular, purity) than the Ra—Ac solution (1);

a step (IV) of allowing the actinium radioisotopes contained in the Ac solution (2) other than $^{225}$Ac to decay to obtain a Ra—Ac solution (3) containing radium isotopes (Ra) resulting from decay; and a step (V) of separating Ra and Ac contained in the Ra—Ac solution (3) to obtain an Ac solution (4) that has a higher $^{225}$Ac concentration (in particular, purity) than the Ra—Ac solution (3), in which the Ac solution (4) is used for producing a medicine indicated in (a) or (b) below:

(a) a medicine that contains, as an active ingredient, a conjugate between a chelating agent that has formed a complex with $^{225}$Ac, and an Nd2 antibody (b) a medicine that contains, as an active ingredient, a conjugate between a chelating agent that has formed a complex with $^{225}$Ac, and a targeting agent (excluding the Nd2 antibody).

In the present description, for example, actinium having a mass number of 225 is described as $^{225}$Ac, and, for example, actinium radioisotopes and other radioisotopes that do not have to be distinguished are described as Ac. The same applies to radium and other elements.

<Step (I)>

In the step (I), a $^{226}$Ra target is irradiated with at least one type of particles selected from protons, deuterons, neutrons, and photons to generate two or more actinium radioisotopes (Ac) including at least $^{225}$Ac. Ac is generated, in some cases, via decay, for example, by irradiating a $^{226}$Ra target with particles.

Examples of the two or more actinium radioisotopes (Ac) including at least $^{225}$Ac are $^{225}$Ac and at least one selected from $^{224}$Ac and $^{226}$Ac.

The $^{226}$Ra target may be any target that contains $^{226}$Ra, but preferably $^{226}$Ra is immobilized on a substrate.

One example of the method for preparing a $^{226}$Ra target is a method that involves allowing $^{226}$RaCO$_3$ to deposit on a silicon carbide (SiC) filter and performing filtration to prepare a Ra target having a particular thickness; however, from the viewpoint of capability to prepare a Ra target efficiently by remote control also, an electrodeposition method that involves electrically immobilizing free Ra in the solution onto a substrate is preferable. An example of the electrodeposition method is described in JPA 2007-508531, in which a radium-containing substance is electrodeposited on an aluminum substrate from one organic aqueous solution containing radium ions; however, from the viewpoint of increasing the electrodeposition efficiency without application of high voltage, a method that involves performing electrodeposition on a substrate by using an electrodeposition solution containing a pH buffer is more preferable. One example of such a technique is disclosed in International Publication No. 2020/256066 filed by one of the applicants of the present application.

During the irradiation described above, specifically, particles are preferably accelerated by using an accelerator such as cyclotron or a linear accelerator, preferably a cyclotron, and the $^{226}$Ra target is preferably irradiated with such accelerated particles.

The particles are preferably protons, deuterons, or photons, and more preferably protons. For example, when protons are used as the particles for irradiation, a $^{226}$Ra (p, 2n)$^{225}$Ac nuclear reaction occurs, and $^{224}$Ac and/or $^{226}$Ac is generated as impurities. Alternatively, when photons (gamma particles) are used as the particles for irradiation, a $^{226}$Ra (gamma, n)$^{225}$Ra nuclear reaction occurs, and $^{225}$Ra decays and generates $^{225}$Ac. When protons, deuterons, or photons are used as the particles, $^{227}$Ac (half-life: 27 years) is not generated in theory; thus, these particles are preferable from the viewpoint of obtaining an $^{225}$Ac solution having a high $^{225}$Ac concentration (in particular, purity).

The conditions for particle irradiation are not particularly limited as long as the type of particles, energy, irradiation time, and other factors are appropriately adjusted to generate two or more actinium radioisotopes (Ac) including at least $^{225}$Ac, and various conditions may be employed.

As $^{225}$Ac and the particles undergo a nuclear reaction, usually, nuclear fission of $^{226}$Ra occurs as a side reaction, and $^{140}$Ba is generated.

Furthermore, the raw materials for the $^{226}$Ra target usually contain, in addition to $^{226}$Ra, Ba, and a technique that separates $^{226}$Ra and Ba has been developed as disclosed in PTL 1; however, since it is difficult to completely remove Ba from the $^{226}$Ra target, a nuclear reaction between Ba contained in the $^{226}$Ra target and, among the aforementioned particles, protons used as the particles occurs and generates $^{132}$La (half-life: 4.8 hours) and $^{135}$La (half-life: 19.5 hours).

In one embodiment of the present invention, these foreign radionuclides are sequentially removed in the steps described below.

<Step (II)>

In the step (II), the $^{226}$Ra target after the step (I) is dissolved to obtain a Ra—Ac solution (1) that contains $^{226}$Ra and Ac.

The Ra—Ac solution (1) obtained not long after completion of the step (I) contains, for example, $^{224}$Ac, $^{225}$Ac, $^{226}$Ac, $^{226}$Ra, $^{140}$Ba, $^{132}$La, and $^{135}$La.

In dissolving the $^{226}$Ra target, an acid may be used. One acid or two or more acids may be used.

Examples of the acid include inorganic acids such as nitric acid, hydrochloric acid, phosphoric acid, sulfuric acid, boric acid, and hydrofluoric acid. Among these, from the viewpoints of, for example, the capability to sufficiently dissolve $^{226}$Ra and Ac and efficiently carry out the step (III) described below, nitric acid and hydrochloric acid are preferable, and nitric acid is particularly preferable.

In order to dissolve the $^{226}$Ra target, the amount of the acid used is preferably at least 10 times and more preferably at least 20 times the molar amount of $^{226}$Ra and is preferably at most 50 times and more preferably at most 40 times the molar amount of $^{226}$Ra.

<Step (III)>

In the step (III), $^{226}$Ra and Ac contained in the Ra—Ac solution (1) and originating from the $^{226}$Ra target are separated to obtain an Ac solution (2) that has a higher Ac concentration (in particular, purity) than the Ra—Ac solution (1).

This step (III) can obtain, for example, an Ac solution (2) that contains $^{224}$Ac, $^{225}$Ac, and $^{226}$Ac and a Ra solution (2) that contains $^{226}$Ra and $^{140}$Ba. In the step (III), for example, $^{226}$Ra and $^{140}$Ba can be separated and removed from the Ra—Ac solution (1) that contain $^{224}$Ac, $^{225}$Ac, $^{226}$Ac, $^{226}$Ra, and $^{140}$Ba; thus, the Ac solution (2) acquires a higher Ac concentration (in particular, purity) than the Ra—Ac solution (1).

When the time from the completion of the step (I) to the start of the step (III) is represented by T1, T1 is preferably as short as possible, the lower limit of the time T1 may be the shortest time the step (II) can be carried out, and the time T1 is preferably shorter than 7 days and more preferably 5 days or shorter.

When T1 is within the aforementioned range, the Ac and $^{140}$Ba can be separated in the early stage, and thus an Ac solution (2) containing less $^{140}$La generated by decay of $^{140}$Ba can be easily obtained.

In addition, when T1 is within the aforementioned range, the Ra solution (2) obtained can be re-used promptly.

The amount of $^{225}$Ac generated from the $^{226}$Ra target is trace, and most $^{226}$Ra remains unreacted; however, since $^{226}$Ra is a precious nuclide and is not easy to discard, the Ra solution (2) is preferably recovered and reused. The Ra solution (2) is, for example, subjected to a purifying step as necessary and then reused as, for example, an electrodeposition solution for producing a $^{226}$Ra target. One example of such a technique is disclosed in International Publication No. 2021/002275 filed by one of the applicants of the present application.

In a conventional method, the $^{226}$Ac content needs to be sufficiently decreased in carrying out the step (III); thus, when Ra and Ac are separated after the $^{226}$Ac content in the Ra—Ac solution (1) is sufficiently decreased, the obtained Ac fraction contains a corresponding amount of $^{140}$La, and a more time has been needed to decrease this $^{140}$La content.

When the time required is this long, the amount of desirable $^{225}$Ac decreases over time, and thus it has been difficult for this conventional method to produce an $^{225}$Ac solution having a high $^{225}$Ac concentration (in particular, purity) while suppressing the loss caused by radio-active decay of $^{225}$Ac or to produce an $^{225}$Ac solution that achieves both a low $^{140}$La content and a high $^{225}$Ac concentration (in particular, purity).

Moreover, as described above, most $^{226}$Ra does not transform into $^{225}$Ac and remains as $^{226}$Ra, which is efficiently recovered and recycled as a raw material for $^{225}$Ac; however, according to the conventional method, $^{226}$Ra could not be reused until after the time taken for the $^{226}$Ac content to sufficiently reduce has elapsed.

However, according to the present production method, an $^{225}$Ac solution having a high $^{225}$Ac concentration (in particular, purity) can be easily obtained, and, in addition, $^{226}$Ra can be immediately reused after performing the step (III); thus, the use efficiency of $^{226}$Ra can be enhanced.

In the step (III), any technique that can separate $^{226}$Ra and Ac can be employed, and preferable examples thereof include a technique of using a Ra-capturing solid-phase extraction agent and a technique of colloidizing Ac.

An example of the solid-phase extraction agent is at least one selected from a cation-exchange resin, a solid-phase extraction agent (a) containing a compound represented by formula (A) below, a solid-phase extraction agent (b) containing a compound represented by formula (B) below, and a solid-phase extraction agent (c) containing a compound represented by formula (C) below.

In the step (III), separation of Ra and Ac may be performed twice or more. For example, when a cation-exchange resin is used, separation may be performed twice or more by using the same cation-exchange resin, different cation-exchange resins, or a cation-exchange resin and, for example, a solid-phase extraction agent (a). In such a case, the order in which the cation-exchange resin and the solid-phase extraction agent (a) are used is not particularly limited. This description regarding the use of the cation-exchange resin equally applies to the case in which the solid-phase extraction agent (a), (b), or (c) is used.

After separation of Ra and Ac, a washing step of washing the cation-exchange resin and/or the solid-phase extraction agent is preferably performed.

From the viewpoint of, for example, the capability to easily obtain an Ac solution (2) having a high Ac purity from the Ra—Ac solution (1) with a smaller amount of the solvent used, the step (III) preferably involves separating Ra and Ac by using a solid-phase extraction agent (a) among these, and then separating Ra and Ac by using the solid-phase extraction agent (b).

Alternatively, the step (III) can involve alkalizing the Ra—Ac solution (1), filtering the alkalized Ra—Ac solution (1) through, for example, a membrane filter to collect colloidized actinium hydroxide on the filter and obtain a solution that serves as a Ra solution (2), and dissolving Ac captured on the filter to obtain an Ac solution (2).

Cation-Exchange Resin

Examples of the cation-exchange resin include a strong acid cation-exchange resin, and an example of the commercially available product of the cation-exchange resin is "AG50W" produced by Bio-Rad Laboratories, Inc.

From the viewpoint of capability to efficiently separate Ra and Ac, for example, the cation-exchange resin is preferably a resin that has a function of selectively adsorbing divalent cations (hereinafter, this resin may also be referred to as the "resin (i)").

A specific example of the step (III) when the resin (i) is used is a method that involves bringing the Ra—Ac solution (1) into contact with the resin (i) under alkaline conditions to allow the resin (i) to adsorb Ra ions and to thereby obtain a flow-through fraction that serves as an Ac solution (2), and then allowing the Ra ions to elute from the resin (i) under acidic conditions to obtain a Ra solution (2).

The resin (i) is preferably a resin that can form a complex with a metal ion under alkaline conditions and can elute the metal ion under acidic conditions, and an example thereof is a resin that has a divalent cation-exchange group. Examples of the divalent cation-exchange group include an iminodiacetic acid group, a polyamine group, and a methylglycan group, and an iminodiacetic acid group is preferable.

A more preferable example of the resin (i) is a styrenedivinylbenzene copolymer having an iminodiacetic acid group. Examples of the commercially available product of the resin having an iminodiacetic acid group include "Chelex" series produced by Bio-Rad Laboratories, Inc., "DIAION" series produced by Mitsubishi Chemical Corporation, and "Amberlite" series produced by The Dow Chemical Company, and, a more specific example thereof is "Chelex 100" (particle diameter: 50 to 100 mesh, ionic form: Na form, Fe form) produced by Bio-Rad Laboratories, Inc.

The resin (i) may be packed into a tube and used. The tube may be any flexible tube that can be packed with the resin (i), but is preferably a flexible tube composed of rubber or resin, for example, and is more preferably a medical tube.

Such a tube is preferable since, when such a tube is used, the length can be longer than typical glass columns, in other words, the number of theoretical plates can be increased, and the Ra ion adsorption efficiency can be increased. In addition, the resin (i) after the radioactive substances have been run can be easily discarded as packed in the tube without causing radioactive contamination on other instruments and devices, for example.

Solid-Phase Extraction Agent (a)

The solid-phase extraction agent (a) may be any agent that contains a compound represented by formula (A) below, and may further contain known components contained in solid-phase extraction agents.

The solid-phase extraction agent (a) may be solely composed of a compound represented by formula (A), or may contain a compound represented by formula (A) below and other components (for example, known additives and inactive supports) (including a solid-phase extraction agent that contains an inactive support and a compound represented by formula (A) below introduced into the inactive support).

The solid-phase extraction agent (a) may contain one or more compounds represented by formula (A) below.

The solid-phase extraction agent (a) is preferably an inactive support that contains a compound represented by formula (A) below, and more preferably a porous silica or an organic polymer that contains a compound represented by formula (A) below. The pore size of the porous silica is not particularly limited but is preferably about 50 to 150 μm in diameter.

A specific example of the step (III) using the solid-phase extraction agent (a) is a method that involves running a Ra—Ac solution (1) containing a high concentration acid (for example, 0.3 M or higher for nitric acid) through the solid-phase extraction agent (a) so that Ac ions are selectively retained on the solid-phase extraction agent (a) and the flow-through fraction is obtained as a Ra solution (2), and running a low concentration acid through the solid-phase extraction agent (a) retaining the Ac ions so as to elute the Ac ions retained thereto and obtain an Ac solution (2).

As described above, the concentration of the acid used to separate Ra and Ac (allowing Ac ions to be retained on the solid-phase extraction agent (a) and allowing Ra ions to pass) by using the solid-phase extraction agent (a) is high; thus, by using the solid-phase extraction agent (a) in the step (III), the Ra ions and the Ac ions can be satisfactorily separated even when the amount of the solvent used for separating the Ac ions from the solution containing Ra and Ac ions is small.

Examples of the high concentration acid used with the solid-phase extraction agent (a) are the same as those for the acid used in the Ra—Ac solution (1) described above, and preferable acids are also the same. One acid or two or more acids may be used.

When nitric acid is used as the high concentration acid used with the solid-phase extraction agent (a), the concentration thereof is preferably 0.3 M or higher and more preferably 0.5 M or higher, and is preferably 4.0 M or lower, and when hydrochloric acid is used as the acid, the concentration is preferably 1 M or higher and 8 M or lower from the viewpoint of more efficiently separating Ra and Ac (separating Ac and Ra with a smaller amount of Ac flowing through and a smaller amount of Ra retained), for example.

The flow rate of the Ra—Ac solution (1) running through the solid-phase extraction agent (a) is preferably 0.01 mL/min or more, more preferably 0.1 mL/min or more, and yet more preferably 0.5 mL/min or more, and is preferably 5 mL/min or less, more preferably 3 mL/min or less, and yet more preferably 2 mL/min or less from the viewpoint of more efficiently separating Ra and Ac, for example.

Examples of the low concentration acid used with the solid-phase extraction agent (a) are the same as those for the acid used in the Ra—Ac solution (1) described above, and preferable acids are also the same. One acid or two or more acids may be used.

The concentration of the low concentration acid used with the solid-phase extraction agent (a) is not particularly limited as long as the retained Ac ions can be sufficiently eluted from the solid-phase extraction agent (a); however, when the same acid as that used with the Ra—Ac solution (1) described above is used as the acid, the difference in concentration is preferably large.

When nitric acid is used as the low concentration acid used with the solid-phase extraction agent (a), the concentration thereof is preferably higher than 0 M and preferably 0.2 M or lower, more preferably 0.1 M or lower, and yet more preferably 0.01 M or lower, and when hydrochloric acid is used as the acid, the concentration thereof is preferably higher than 0 M and 0.2 M or lower.

In addition, since there is a possibility that the acid used in the Ra—Ac solution (1) would remain in the solid-phase extraction agent (a), in order to elute Ac ions from the solid-phase extraction agent (a) without fail, for example, the concentration of the high concentration acid preferably differs from the concentration of the low concentration acid, and the concentration of the high concentration acid is preferably 15 or more provided that the concentration of the low concentration acid is 1.

The flow rate of the low concentration acid used with the solid-phase extraction agent (a) is preferably 0.1 mL/min or more and more preferably 0.5 mL/min or more, and preferably 20 mL/min or less and more preferably 10 mL/min or less from the viewpoint of capability to sufficiently elute the retained Ac ions from the solid-phase extraction agent (a), for example.

The solid-phase extraction agent (a) is not particularly limited, and, for example, a commercially available product may be used. Examples thereof include "DGA Resin" and "DGA Branched Resin" produced by Eichrom Technologies Inc.

(A)

In formula (A), m and n each independently represent 0 or 1, and preferably 1.

In formula (A), $R^1$ to $R^4$ each independently represent an alkyl group having 8 to 12 carbon atoms. The alkyl group may be linear or branched. $R^1$ to $R^4$ preferably each independently represent an octyl group or a 2-ethylhexyl group.

Solid-Phase Extraction Agent (b)

The solid-phase extraction agent (b) may be any agent that contains a compound represented by formula (B) below, and may further contain known components contained in solid-phase extraction agents.

The solid-phase extraction agent (b) may be solely composed of a compound represented by formula (B), or may contain a compound represented by formula (B) below and other components (for example, known additives and inactive supports) (including a solid-phase extraction agent that contains an inactive support and a compound represented by formula (B) introduced into the inactive support).

The solid-phase extraction agent (b) may contain one or more compounds represented by formula (B) below.

The solid-phase extraction agent (b) is preferably an inactive support that contains a compound represented by formula (B) below, and more preferably a porous silica or an organic polymer that contains a compound represented by formula (B) below. The pore size of the porous silica is not particularly limited but is preferably about 50 to 150 μm in diameter.

A specific example of the step (III) using the solid-phase extraction agent (b) is a method that involves running a Ra—Ac solution (1) containing a low concentration acid (for example, 0.2 M or lower for nitric acid) through the solid-phase extraction agent (b) so that Ac ions are selectively retained on the solid-phase extraction agent (b) and the flow-through fraction is obtained as a Ra solution (2), and running a high concentration acid through the solid-phase extraction agent (b) retaining the Ac ions so as to elute the Ac ions retained thereto and obtain an Ac solution (2).

Examples of the low concentration acid used with the solid-phase extraction agent (b) are the same as those for the acid used with the Ra—Ac solution (1) described above, and preferable acids are also the same. One acid or two or more acids may be used.

When nitric acid is used as the low concentration acid used with the solid-phase extraction agent (b), the concentration thereof is preferably higher than 0 M and preferably lower than 0.2 M, more preferably 0.1 M or less, and yet more preferably 0.01 M or less from the viewpoint of more efficiently separating Ra and Ac (separating Ac and Ra with a smaller amount of Ac flowing out and a smaller amount of Ra retained), for example, and when hydrochloric acid is used as the acid, the concentration thereof is preferably higher than 0 M and 0.2 M or lower.

The flow rate of the Ra—Ac solution (1) running through the solid-phase extraction agent (b) is preferably 1 mL/min or more and more preferably 1.5 mL/min or more, and preferably 30 mL/min or less and more preferably 20 mL/min or less from the viewpoint that the Ac ions can be sufficiently retained on the solid-phase extraction agent (b), for example.

Examples of the high concentration acid used with the solid-phase extraction agent (b) are the same as those for the acid used with the Ra—Ac solution (1) described above, and preferable acids are also the same. One acid or two or more acids may be used.

When nitric acid is used as the high concentration acid used with the solid-phase extraction agent (b), the concentration thereof is preferably 0.2 M or higher, more preferably 0.3 M or higher, and yet more preferably 0.5 M or higher, and preferably 4 M or lower, more preferably 2 M or lower, and yet more preferably 1 M or lower, and when hydrochloric acid is used as the acid, the concentration thereof is preferably 0.3 M or higher and 8 M or lower.

The flow rate of the high concentration acid used with the solid-phase extraction agent (b) is preferably 0.5 mL/min or more, more preferably 1 mL/min or more, and yet more preferably 2 mL/min or more, and preferably 30 mL/min or less, more preferably 25 mL/min or less, and yet more preferably 20 mL/min or less from the viewpoint of capability to sufficiently elute the retained Ac ions from the solid-phase extraction agent (b).

The solid-phase extraction agent (b) is not particularly limited, and, for example, a commercially available product may be used. Examples thereof include "Ln Resin", "Ln2 Resin", and "Ln3 Resin" produced by Eichrom Technologies Inc.

In formula (B), $R^5$ and $R^6$ each independently represent —R' or —OR' (R' represents an alkyl group having 8 carbon atoms). The alkyl group having 8 carbon atoms represented by R' may be linear or branched, and preferable examples thereof include an octyl group, a 2-ethylhexyl group, and 2-methyl-4,4-dimethylpentyl group.

Preferable examples of the compound represented by formula (B) are compounds represented by following formulae (B-1) to (B-3).

Solid-Phase Extraction Agent (c)

The solid-phase extraction agent (c) may be any agent that contains a compound represented by formula (C) below, and may further contain known components contained in solid-phase extraction agents.

The solid-phase extraction agent (c) may be solely composed of a compound represented by formula (C), or may contain a compound represented by formula (C) below and other components (for example, a compound represented by $R^{10}$—OH ($R^{10}$ represents an alkyl group having 4 to 12 carbon atoms and preferably represents an octyl group), a known additive, and an inactive support) (including a solid-phase extraction agent that contains an inactive support and a compound represented by formula (C) introduced into the inactive support).

The solid-phase extraction agent (c) may contain one or more compounds represented by formula (C) below.

The solid-phase extraction agent (c) is preferably an inactive support that contains a compound represented by formula (C) below, and more preferably a porous silica or an organic polymer that contains a compound represented by formula (C) below. The pore size of the porous silica is not particularly limited but is preferably about 50 to 150 μm in diameter.

A specific example of the step (III) using the solid-phase extraction agent (c) is a method that involves running a Ra—Ac solution (1) containing a high concentration acid through the solid-phase extraction agent (c) so that $^{226}$Ra ions are selectively retained on the solid-phase extraction agent (c) and the flow-through fraction is obtained as an Ac solution (2), and running a low concentration acid through the solid-phase extraction agent (c) retaining the $^{226}$Ra ions so as to elute the $^{226}$Ra ions retained thereto and obtain a Ra solution (2).

Examples of the high concentration acid used with the solid-phase extraction agent (c) are the same as those for the acid used in the Ra—Ac solution (1) described above, and preferable acids are also the same. One acid or two or more acids may be used.

When nitric acid is used as the high concentration acid used with the solid-phase extraction agent (c), the concentration thereof is preferably higher than 0.1 M and more preferably 1 M or higher, and preferably 8 M or lower and more preferably 4 M or lower.

Examples of the low concentration acid used with the solid-phase extraction agent (c) are the same as those for the acid used in the Ra—Ac solution (1) described above, and preferable acids are also the same. One acid or two or more acids may be used.

When nitric acid is used as the low concentration acid used with the solid-phase extraction agent (c), the concentration thereof is preferably higher than 0 M and preferably 0.1 M or lower and more preferably 0.05 M or lower.

The solid-phase extraction agent (c) is not particularly limited, and, for example, a commercially available product may be used. Examples thereof include "Sr Resin" produced by Eichrom Technologies Inc.

(C)

In formula (C), R8 to R9 each independently represent a hydrogen atom or an alkyl group having 1 to 6 carbon atoms. The alkyl group may be linear or branched, and a preferable example thereof is a t-butyl group.

<Step (IV)>

In the step (IV), actinium radioisotopes contained in the Ac solution (2) other than $^{225}$Ac are allowed to decay to obtain a Ra—Ac solution (3) containing radium isotopes (Ra) resulting from decay.

As a result of the step (IV), a Ra—Ac solution (3) preferably containing $^{225}$Ac, $^{224}$Ra, and $^{226}$Ra is obtained.

Here, "allowing actinium radioisotopes other than $^{225}$Ac to decay" means that the actinium radioisotopes contained in the Ac solution (2) other than $^{225}$Ac, specifically, one or both of $^{224}$Ac and $^{226}$Ac, are allowed to decay to generate radium isotopes (Ra). $^{224}$Ac decays and forms $^{224}$Ra (half-life: 3.66 days). $^{226}$Ac decays and forms $^{226}$Ra and $^{226}$Th (half-life: 30.9 minutes). In the step (IV), $^{224}$Ac and $^{226}$Ac may be allowed to decay partly, but it is preferable that $^{224}$Ac and $^{226}$Ac be sufficiently decayed.

When the time from after completion of the step (III) to the start of the step (V) described below is represented by T2, T2 is preferably longer than T1, in other words, the relationship, T2>T1 is preferably satisfied, and more preferably the relationship, T2≥2×T1, is satisfied.

The lower limit of T2 is preferably the time sufficient for $^{226}$Ac to decay. In this manner, radium isotopes can be generated from $^{224}$Ac and $^{226}$Ac, and $^{226}$Th can be eliminated.

The upper limit of T2 is preferably set from the viewpoint of suppressing the loss of $^{225}$Ac as much as possible.

For example, when T2 is 20 days, a simulation using PHITS simulation code predicts 1×10$^{-5}$ or less of $^{226}$Ac. Note that the simulation has predicted the numerical values of other foreign radionuclides after elapse of any desired time based on the assumption that the radioactivity of $^{225}$Ac upon completion of irradiation in the step (I) is 1.

When $^{140}$Ba has decayed to $^{140}$La during the period from the step (I) to the step (III), it is possible that $^{140}$La mixes into the Ac solution (2). If $^{140}$La affects the quality of the Ac solution (4) obtained in the step (V) described below, the step (IV) may be used as a step for removing $^{140}$La in the Ac solution (2). In such a case, T2 can be set so that, at seven days after completion of the step (V) described below, the $^{140}$La content/$^{225}$Ac content is preferably 1×10$^{-5}$ or less, more preferably 1×10$^{-6}$ or less, and yet more preferably 1×10$^{-7}$ or less.

When T2 is set as such, foreign nuclides such as $^{132}$La (half-life: 4.8 hours) and $^{135}$La (half-life: 19.5 hours) generated in the step (I) can be eliminated. In the conventional method, one conceivable method for reducing $^{132}$La and $^{135}$La is to reduce the Ba content in the $^{226}$Ra target; however, by adjusting T2 to be within the aforementioned range, an $^{225}$Ac solution (4) having a low La content can be obtained irrespective of the Ba content in the $^{226}$Ra target. Thus, according to the present production method in which T2 is within the aforementioned range, no limit is imposed on the $^{226}$Ra target to be used, and the flexibility of selecting the $^{226}$Ra target is high.

<Step (V)>

In the step (V), Ra and Ac contained in the Ra—Ac solution (3) are separated to obtain an Ac solution (4) that has a higher $^{225}$Ac purity than the Ra—Ac solution (3).

The Ac solution (4) has a higher $^{225}$Ac concentration (in particular, purity) than the Ra—Ac solution (3) since, for example, $^{224}$Ra and $^{226}$Ra can be separated and removed from the Ra—Ac solution (3) that contains $^{225}$Ac, $^{224}$Ra, and $^{226}$Ra.

An example of the specific method used in the step (V) is the same as in the step (III).

The period from the step (I) to completion of the step (V) can be, for example, one month.

<Medicine>

The Ac solution (4) obtained in the step (V) is used to produce a medicine indicated in (a) or (b) below.

This medicine is (a) a medicine that contains, as an active ingredient, a conjugate between a chelating agent that has formed a complex with $^{225}$Ac, and an Nd2 antibody, or (b)

a medicine that contains, as an active ingredient, a conjugate between a chelating agent that has formed a complex with $^{225}$Ac, and a targeting agent (excluding the Nd2 antibody).

The chelating agent may be any compound capable of forming a complex with $^{225}$Ac, and examples thereof include compounds below and compounds that include structures derived from such compounds.

DOTA (1,4,7,10-tetraazacyclododecane-1,4,7,10-tetraacetic acid)

DOTMA ((1R, 4R, 7R, 10R)-α,α',α'',α'''-tetramethyl-1,4,7,10-tetraazacyclododecane-1,4,7,10-tetraacetic acid)

DOTAM (1,4,7,10-tetrakis(carbamoylmethyl)-1,4,7,10-tetraazacyclododecane)

DOTA-GA (α-(2-carboxyethyl)-1,4,7,10-tetraazacyclododecane-1,4,7,10-tetraacetic acid)

DOTP (((1,4,7,10-tetraazacyclododecane-1,4,7,10-tetrayl)tetrakis(methylene))tetraphosphonic acid)

DOTMP (1,4,7,10-tetraazacyclododecane-1,4,7,10-tetrakis(methylenephosphonic acid))

DOTA-4AMP (1,4,7,10-tetraazacyclododecane-1,4,7,10-tetrakis(acetamidomethylenephosphonic acid)

DO2P (tetraazacyclododecane dimethanephosphonic acid)

The Nd2 antibody may be any antibody originating from Nd2, which is a type of antibody that specifically binds mucin subtype 5AC, and may be a monoclonal antibody, a polyclonal antibody, a murine antibody, a chimeric antibody, or a humanized antibody. Examples of such Nd2 antibodies include murine antibodies described in Japanese Journal of Cancer Research, 87, 977-984, 199, chimeric antibodies described in JPA 1995-203974 and JPA 1999-5749, and humanized antibodies described in International Publication Nos. 2013/157102 and 2013/157105.

The targeting agent refers to an agent other than the Nd2 antibodies, the agent having a chemical structure for expressing directionality for a target organ or tissue in a living body or a specificity to a target molecule. In the present description, the target organ, tissue, or molecule is generally referred to as a "target site".

The targeting agent is preferably at least one selected from the group consisting of a linear peptide, a cyclic peptide, a combination of these, a protein, an antibody (excluding Nd2 antibodies) and a fragment thereof, a growth factor, an affibody, a unibody, a nanobody, a monosaccharide, a polysaccharide, a vitamin, an antisense nucleic acid, siRNA, miRNA, a nucleic acid aptamer, a decoy nucleic acid, a cPG oligonucleic acid, a peptide nucleic acid, a liposome, a micelle, nanoparticles, and carbon nanotubes, and is more preferably a polypeptide.

The targeting agent is preferably a targeting agent composed of an amino acid, and the amino acid constituting the targeting agent may be natural or synthetic, and may have any molecular weight.

The polypeptide may be any peptide constituted by three or more amino acid residues, and specific examples thereof include linear peptides, cyclic peptides, or combinations of these, proteins, and antibodies (excluding Nd2 antibodies) and fragments thereof, e.g., IgG, IgA, IgM, IgD, and IgE-type antibodies (immunoglobulins), antibody fragments such as Fab fragments and F(ab')2 fragments, and peptide aptamers.

When the targeting agent is an antibody (excluding Nd2 antibodies), a murine antibody, a chimeric antibody, or a humanized antibody that has an ability to specifically bind an antigen is preferable, and a humanized antibody is more preferable. The antibody preferably has stable physical properties and good accumulation on the target site. The antibody may be used as an antigen-binding fragment, and such an aspect is included in the aspect of the present invention.

Various peptides other than the antibodies (excluding Nd2 antibodies) that can be used as the targeting agent can be synthesized by a conventional known method, for example, a liquid-phase synthesis method, a solid-phase synthesis method, an automated peptide synthesis method, a genetic recombination method, a phage display method, genetic code reprogramming, and a RaPID (random non-standard peptide integrated discovery) method. In synthesizing various peptides, functional groups of amino acids used may be protected as necessary.

In order to form a conjugate between an Nd2 antibody or a targeting agent, and a chelating agent, for example, a known reaction such as a click reaction can be employed.

In the conjugate, the Nd2 antibody and the targeting agent may directly bond with the chelating agent or may indirectly bond with the chelating agent via a known linker structure such as PEG.

In addition, in the conjugate, the Nd2 antibody and the targeting agent may each be modified with a reactive atomic group that can bond with other structures, and then be conjugated with the chelating agent.

The Fc region of the antibody can be site-specifically modified by using, for example, the technology disclosed in International Publication No. 2016/186206 as the method for conjugating an Nd2 antibody or an IgG antibody serving as targeting agent with a chelating agent.

The conjugate formation described above may involve allowing a chelating agent and $^{225}$Ac to form a complex, and then conjugating the resulting complex with an Nd2 antibody or a targeting agent, or, when the chelating agent has bonded with an Nd2 antibody or a targeting agent in advance, may involve allowing this chelating agent to form a complex with $^{225}$Ac.

A method described in International Publication No. 2021/075546 filed by one of the present applicants can be employed as the conjugate formation method described above, for example. In this method, a click-reactive atomic group as a reactive atomic group is introduced into each of an Nd2 antibody or a targeting agent, and a chelating agent in advance, and after $^{225}$Ac is coordinated with the chelating agent, a click reaction is carried out to form a conjugate between the chelating agent that has formed a complex with $^{225}$Ac, and the Nd2 antibody or targeting agent.

Here, the "reactive atomic group" in the present description refers to a chemical structure that directly causes the reaction of bonding one compound with another compound.

The click reaction is, for example, a reaction that occurs by a combination of an alkyne and an azide or a combination of a diene and a dienophile. From the viewpoint of simplicity of the reaction scheme, the click-reactive atomic group is preferably an atomic group that can be used in a metal catalyst-free click reaction. Specific examples of the click reaction that occurs between such a combination of atomic groups include a Huisgen cycloaddition reaction and an inverse electron-demand Diels-Alder reaction.

A triazole skeleton can be formed as a result of the click reaction by introducing, as a click-reactive atomic group, an alkyne-containing atomic group into one of the Nd2 antibody or targeting agent and the chelating agent, and introducing an azide-containing atomic group into the other. A pyridazine skeleton can be formed as a result of the click reaction by introducing a 1,2,4,5-tetrazine-containing atomic group into one of the Nd2 antibody or targeting agent and the chelating agent, and introducing an alkene (dienophile)-containing atomic group into the other.

Specific examples of the click-reactive atomic group include an atomic group that contains dibenzocyclooctyne (DECO) as an alkyne, an atomic group that contains an azide group as an azide, an atomic group that contains 1,2,4,5-tetrazine as a diene, and an atomic group that contains trans-cyclooctene (TCO) as an alkene (dienophile). The click-reactive atomic group can be introduced by using various commercially available reagents. Specifically, when introducing, as the click-reactive atomic group, an atomic group that contains dibenzocyclooctyne (DECO), DECO reagents such as DECO-C6-acid, DECO-amine, DECO-maleimide, DECO-PEG acid, DECO-PEG-NHS ester, DECO-PEG-alcohol, DECO-PEG-amine, DECO-PEG-NH-Boc, carboxyrhodamine-PEG-DECO, sulforhodamine-PEG-DECO, TAMRA-PEG-DECO, DECO-PEG-biotin, DECO-PEG-DECO, DECO-PEG-maleimide, TCO-PEG-DECO, and DECO-mPEG can be used.

[Dissolution and Purification Liquid]

Another embodiment of the present invention is a dissolution and purification liquid obtained by dissolving the $^{226}$Ra target irradiated with particles (for example, at least one type of particles selected from protons, deuterons, neutrons, and photons) and purifying the resulting solution.

The ratio ($^{140}$La content/$^{225}$Ac content) of the $^{140}$La content to the $^{225}$Ac content in the dissolution and purification liquid one month after irradiation with particles is $1\times10^{-5}$ or less, preferably $1\times10^{-6}$ or less, and more preferably $1\times10^{-7}$ or less.

Such a dissolution and purification liquid has a low $^{140}$La content and a high $^{225}$Ac concentration (in particular, purity).

The dissolution and purification liquid can be, specifically, the Ac solution (4) produced by the present production method.

Specifically, the dissolution and purification liquid is preferably used to produce a medicine indicated in (a) or (b) above.

[Method for Producing Medicine]

A method for producing a medicine according to another embodiment of the present invention includes the following step (VIa).

Step (VIa): a step of allowing a chelating agent to form a complex with $^{225}$Ac by using the $^{225}$Ac solution obtained by implementing the present production method.

The reaction of allowing the chelating agent to form a complex with $^{225}$Ac can be carried out in the presence of any desired solvent under heating as appropriate, for example. Examples of such a reaction include the reactions described in International Publication No. 2021/033530 and International Publication No. 2021/075546 filed by one of the applicants of the present application.

The step (VIa) may further include a step of forming a conjugate between the chelating agent that has formed a complex with $^{225}$Ac, and an Nd2 antibody or a targeting agent, and preferably includes this step.

Examples of the step for forming the conjugate include the same steps as those described in the section describing the present production method.

The step (VIa) may further include a medicine formulation step for obtaining a medicine that contains, as an active ingredient, a conjugate between a chelating agent that has formed a complex with $^{225}$Ac, and an Nd2 antibody or a targeting agent.

The medicine formulation step may involve, as appropriate, adding various additives such as a pH adjustor, e.g., a citric acid buffer, a phosphoric acid buffer, or a boric acid buffer, a solubilizer such as polysorbate, a stabilizer, and an antioxidant, or adjusting the radiation concentration by dilution with an isotonic liquid such as water or physiologic saline.

The medicine formulation step may also include a step of performing sterile filtration with, for example, a membrane filter after addition of additives or concentration adjustment so as to prepare an injection.

Other Embodiments of the Present Invention

Other embodiments of the present invention include the $^{225}$Ac solution production methods and the dissolution and purification liquid related to the following [1] to [7].

[1] A method for producing an $^{225}$Ac solution, the method including:

a step (I) of irradiating a $^{226}$Ra target with at least one type of particles selected from protons, deuterons, neutrons, and photons to generate two or more actinium radioisotopes (Ac) including at least $^{225}$Ac;

a step (II) of dissolving the $^{226}$Ra target after the step (I) to obtain a Ra—Ac solution (1) that contains $^{226}$Ra and Ac;

a step (III) of separating $^{226}$Ra and Ac originating from the $^{226}$Ra target and contained in the Ra—Ac solution (1) to obtain an Ac solution (2) that has a higher Ac concentration (in particular, purity) than the Ra—Ac solution (1);

a step (IV) of allowing the actinium radioisotopes contained in the Ac solution (2) other than $^{225}$Ac to decay to obtain a Ra—Ac solution (3) containing radium isotopes (Ra) resulting from decay; and a step (V) of separating Ra and Ac contained in the Ra—Ac solution (3) and to obtain an Ac solution (4) that has a higher $^{225}$Ac concentration (in particular, purity) than the Ra—Ac solution (3).

[2] The method for producing an $^{225}$Ac solution described in [1], in which when a time from completion of the step (I) to start of the step (III) is represented by T1 and a time from completion of the step (III) to start of the step (V) is represented by T2, T1 and T2 satisfy a relationship of T2>T1.

[3] The method for producing an $^{225}$Ac solution described in [1] or [2] above, in which a ratio ($^{140}$La content/$^{225}$Ac content) of the $^{140}$La content to the $^{225}$Ac content in the Ac solution (4) is $1\times10^{-5}$ or less at seven days after completion of the step (V).

[4] The method for producing an $^{225}$Ac solution described in [2], in which the time T1 is shorter than seven days.

[5] The method for producing an $^{225}$Ac solution described in any one of [1] to [4], in which, in the step (III) or (V), a solid-phase extraction agent that captures Ra is used or Ac is colloidized.

[6] The method for producing an $^{225}$Ac solution described in [5], in which the solid-phase extraction agent is at least one selected from a cation-exchange resin, a solid-phase extraction agent (a) containing a compound represented by formula (A) above, a solid-phase extraction agent (b) containing a compound represented by formula (B) above, and a solid-phase extraction agent (c) containing a compound represented by formula (C) above.

[7] A dissolution and purification liquid obtained from a $^{226}$Ra target irradiated with particles, in which a ratio ($^{140}$La content/$^{225}$Ac content) of a $^{140}$La content to an $^{225}$Ac content in the dissolution and purification liquid one month after irradiation with particles is $1\times10^{-5}$ or less.

EXAMPLES

Hereinafter, an embodiment of the present invention is more specifically described through Examples which do not limit the present invention in any way.

<Computational Chemistry Technique>

By using simulation code PHITS (particle and heavy ion transport code system), the amounts of radioactive elements contained in each of the solutions described below were calculated by simulation based on the following assumptions.

[Simulation 1]

It was assumed that a step (I) involving irradiating a $^{226}$Ra target (ϕ 20 mm, $^{226}$Ra mass: 50 mg, Ba mass: 50 mg) with protons at an irradiation energy of 16 MeV for 1 hour was performed.

It was assumed that, immediately after completion of the step (I), a step (II) of dissolving the $^{226}$Ra target obtained in the step (I) to obtain a Ra—Ac solution (1) that contained $^{226}$Ra and Ac was performed.

The radiation of $^{225}$Ac ($^{225}$Ac content) in the Ra—Ac solution (1) obtained in the step (II) was standardized as 1.00 (1.00E+00). In this case, it was calculated that, in the obtained Ra—Ac solution (1), the $^{224}$Ac content was 5.05E+01, the $^{226}$Ac content was 1.07E+00, the $^{226}$Ra content originating from $^{226}$Ac excluding $^{226}$Ra originating from the $^{226}$Ra target was 4.53E-09, the $^{140}$Ba content was 3.44E-03, and the $^{140}$La content was 2.89E-05.

It was assumed that a step (III) of separating $^{226}$Ra and Ac originating from the $^{226}$Ra target and contained in the Ra—Ac solution (1) to obtain an Ac solution (2) was performed. The time from completion of the step (I) to the start of the step (III) was set to 6 hours (0.25 days).

It was assumed that, during separation of $^{226}$Ra and Ac, the group 3 elements in the periodic table, lanthanoid elements, and actinoid elements could not be separated from Ac, but all other elements could be separated 100%.

It was calculated that, in the Ac solution (2) obtained in the step (III), the $^{225}$Ac content was 9.83E-01, the $^{224}$Ac content was 1.20E+01, the $^{226}$Ac content was 9.31E-01, the $^{226}$Ra content was 0.00 (the $^{226}$Ra content at the start of the step (III) was 5.50E-08), the $^{140}$Ba content was 0.00 (the $^{140}$Ba content at the start of the step (III) was 3.45E-03), and the $^{140}$La content was 3.67E-04.

It was assumed that a step (IV) of allowing the actinium radioisotopes contained in the Ac solution (2) other than $^{225}$Ac to decay to obtain a Ra—Ac solution (3) containing radium isotopes (Ra) resulting from decay was performed, and then a step (V) of separating Ra and Ac contained in the obtained Ra—Ac solution (3) to obtain an Ac solution (4) was performed. The time from completion of the step (I) to the start of the step (V) was set to 504 hours (21 days).

It was assumed that during separation of Ra and Ac, the group 3 elements in the periodic table, lanthanoid elements, and actinoid elements could not be separated from Ac, but all other elements could be separated 100%.

It was calculated that, in the Ac solution (4) obtained in the step (V), the $^{225}$Ac content was 2.33E-01, the $^{224}$Ac content was 0.00, the $^{226}$Ac content was 6.30E-06, the $^{226}$Ra content was 0.00 (the $^{226}$Ra content at the start of the step (V) was 3.28E-07), and the $^{140}$La content was 6.96E-08.

It was calculated that, in the Ac solution (4) seven days after the step (V) (672 hours (28 days) after completion of the step (I)), the $^{225}$Ac content was 1.44E-01, the $^{224}$Ac content was 0.00, the $^{226}$Ac content was 1.14E-07, the $^{226}$Ra content was 2.20E-12, and the $^{140}$La content was 3.86E-09.

The results are summarized in Table 1 below.

TABLE 1

| Type of solution measured<br>Time from completion of step (I) | Ra-Ac solution (1)<br>0 | Ac solution (2)<br>6 h (0.25 d) | Ac solution (4)<br>504 h (21 d) | Ac solution (4)<br>672 h (28 d) |
|---|---|---|---|---|
| Ac-225 | 1.00E+00 | 9.83E-01 | 2.33E-01 | 1.44E-01 |
| Ac-224 | 5.05E+01 | 1.20E+01 | 0 | 0 |
| Ac-226 | 1.07E+00 | 9.31E-01 | 6.30E-06 | 1.14E-07 |
| Ra-226<br>(originating from Ac-226,<br>excluding Ra from the target) | 4.53E-09 | 5.50E-08 → 0.00 | 3.28E-07 → 0.00 | 2.20E-12 |
| Ba-140 | 3.44E-03 | 3.45E-03 → 0.00 | | |
| La-140 | 2.89E-05 | 3.67E-04 | 6.96E-08 | 3.86E-09 |

[Comparative Simulation 1]

It was assumed that a step (I) involving irradiating a $^{226}$Ra target (ϕ 20 mm, $^{226}$Ra mass: 50 mg, Ba mass: 50 mg) with protons at an irradiation energy of 16 MeV for 1 hour was performed.

It was assumed that, immediately after completion of the step (I), a step (II) of dissolving the $^{226}$Ra target obtained in the step (I) to obtain a Ra—Ac solution (1) that contained $^{226}$Ra and Ac was performed.

The radiation of $^{225}$Ac ($^{225}$Ac content) in the Ra—Ac solution (I) obtained in the step (II) was standardized as 1.00 (1.00E+00). In this case, it was calculated that, in the obtained Ra—Ac solution (1), the $^{224}$Ac content was 5.05E+01, the $^{226}$Ac content was 1.07E+00, the $^{226}$Ra content originating from $^{226}$Ac excluding $^{226}$Ra originating from the $^{226}$Ra target was 4.53E-09, the $^{140}$Ba content was 3.44E-03, and the $^{140}$La content was 2.89E-05.

It was assumed that a step (III) of separating $^{226}$Ra and Ac originating from the $^{226}$Ra target and contained in the Ra—Ac solution (1) to obtain an Ac solution (2) was performed. The time from completion of the step (I) to the start of the step (III) was set to 504 hours (21 days).

It was assumed that, during separation of $^{226}$Ra and Ac, the group 3 elements in the periodic table, lanthanoid elements, and actinoid elements could not be separated from Ac, but all other elements could be separated 100%.

It was calculated that, in the Ac solution (2) obtained in the step (III), the $^{225}$Ac content was 2.33E-01, the $^{224}$Ac content was 0.00, the $^{226}$Ac content was 6.30E-06, the $^{226}$Ra content was 0.00 (the $^{226}$Ra content at the start of the step (III) was 3.82E-07), the $^{140}$Ba content was 0.00 (the $^{140}$Ba content at the start of the step (III) was 1.12E-03), and the $^{140}$La content was 1.29E-03.

It was calculated that, in the Ac solution (2) seven days after the step (III) (672 hours (28 days) after completion of the step (I)), the $^{225}$Ac content was 1.44E-01, the $^{224}$Ac content was 0.00, the $^{226}$Ac content was 1.14E-07, the $^{226}$Ra content was 2.20E-12, and the $^{140}$La content was 7.14E-05.

The results are summarized in Table 2 below.

TABLE 2

| Type of solution measured<br>Time from completion of step (I) | Ra-Ac solution (1)<br>0 | Ac solution (2)<br>504 h (21 d) | Ac solution (2)<br>672 h (28 d) |
|---|---|---|---|
| Ac-225 | 1.00E+00 | 2.33E-01 | 1.44E-01 |
| Ac-224 | 5.05E+01 | 0.00 | 0.00 |
| Ac-226 | 1.07E+00 | 6.30E-06 | 1.14E-07 |
| Ra-226 (originating from Ac-226, excluding Ra from the target) | 4.53E-09 | 3.82E-07 → 0.00 | 2.20E-12 |
| Ba-140 | 3.44E-03 | 1.12E-03 → 0.00 | |
| La-140 | 2.89E-05 | 1.29E-03 | 7.14E-05 |

<Experimental Chemistry Technique>

An $^{225}$Ac solution was produced by the following method.

Example 1

Step (I)

A target constituted by a gold plate (030) with 247 μCi of $^{226}$Ra electrodeposited thereon was irradiated with protons at 18 MeV and 15 ρA for 0.5 hours by using a cyclotron ((p, 2n) reaction).

Step (II)

Three days after irradiation, the irradiated target was dissolved in 16 mL of 0.7 M nitric acid.

Step (III)

The obtained solution was run through a DGA Resin (produced by Eichrom Technologies Inc.) (flow-through fraction (1)). Then the DGA Resin was washed with 5 mL of 0.7 M nitric acid (wash liquid (2)). The flow-through fraction (1) and the wash liquid (2) were deemed to be a $^{226}$Ra recovery fraction and used as an electrodeposition solution for recycling Ra.

Then the DGA Resin was further washed with 15 mL of 0.7 M nitric acid (wash liquid (3)). The wash liquid (3) was discarded.

Next, 20 mL of 0.005 M nitric acid was run through the washed DGA Resin to elute $^{225}$Ac. The eluted $^{225}$Ac was run through an Ln Resin (produced by Eichrom Technologies Inc.) (flow-through fraction (4)). Then the Ln Resin was washed with 10 mL of 0.05 M nitric acid (wash liquid (5)). The flow-through fraction (4) and wash liquid (5) were discarded.

Next, 10 mL of 0.7 M nitric acid was run through the washed Ln Resin to elute $^{225}$Ac ($^{225}$Ac solution (6)). The obtained $^{225}$Ac solution (6) was analyzed with a germanium semiconductor detector, which found 0.2 μCi of $^{225}$Ac in terms of EOB (at the end of bombardment).

Step (IV)

Seventeen days were elapsed after obtaining the $^{225}$Ac solution (6).

Step (V)

After elapse of 17 days described above, 10 mL of the $^{225}$Ac solution (6) was run through the DGA Resin (flow-through fraction (7)). Then the DGA Resin was washed with 20 mL of 0.7 M nitric acid (wash liquid (8)). The flow-through fraction (7) and wash liquid (8) were discarded.

Next, 20 mL of 0.005 M nitric acid was run through the DGA Resin to elute $^{225}$Ac. The eluted $^{225}$Ac was run through the Ln Resin (flow-through fraction (9)). Then the Ln Resin was washed with 10 mL of 0.05 M nitric acid (wash liquid (10)). The flow-through fraction (9) and wash liquid (10) were discarded.

Next, 10 mL of 0.5 M nitric acid was run through the washed Ln Resin to elute $^{225}$Ac ($^{225}$Ac solution (11)). The obtained $^{225}$Ac solution (11) was analyzed with a germanium semiconductor detector, which found 0.2 μCi of $^{225}$Ac in terms of EOB (at the end of bombardment).

Example 2

Production of Ac-225 by Cyclotron Beam Irradiation

Beam irradiation was carried out with a 34 MeV $H_2^+$ (ionized molecular hydrogen) beam provided by NIRS-AVF-930 cyclotron at a nominal intensity of 10 μA for 3 to 5 hours. $H_2^+$ ions were fragmented by the vacuum isolation foil, and a 17 MeV proton beam was obtained at about 20 μA. The SRIM calculation code estimated that the proton energy incident on the target material was 15.6 MeV after the beam had passed through the vacuum foil (Al, 100 μm), the He cooling layer (30 mm), and the target foil (Nb, 50 μm). In order to maximize the expected $^{225}$Ac yield, the on-target proton energy was set to 15.6 MeV to maximize the $^{226}$Ra (p, 2n)$^{225}$Ac reaction cross-section, and this energy value was an intermediate value between the result obtained by ALICE calculation code (maximum of 700 mb at 15 MeV) and the result reported in a previous study, Apostolidis C, Molinet R, McGinley J, Abbas K, Mollenbeck J, Morgenstern A. Cyclotron production of Ac-225 for targeted alpha therapy. Appl Radiat Isot 2005; 62:383-387 (maximum of 710 mb at 16.8 MeV).

Separation of $^{225}$Ac from Target Matrix

Figure 1:
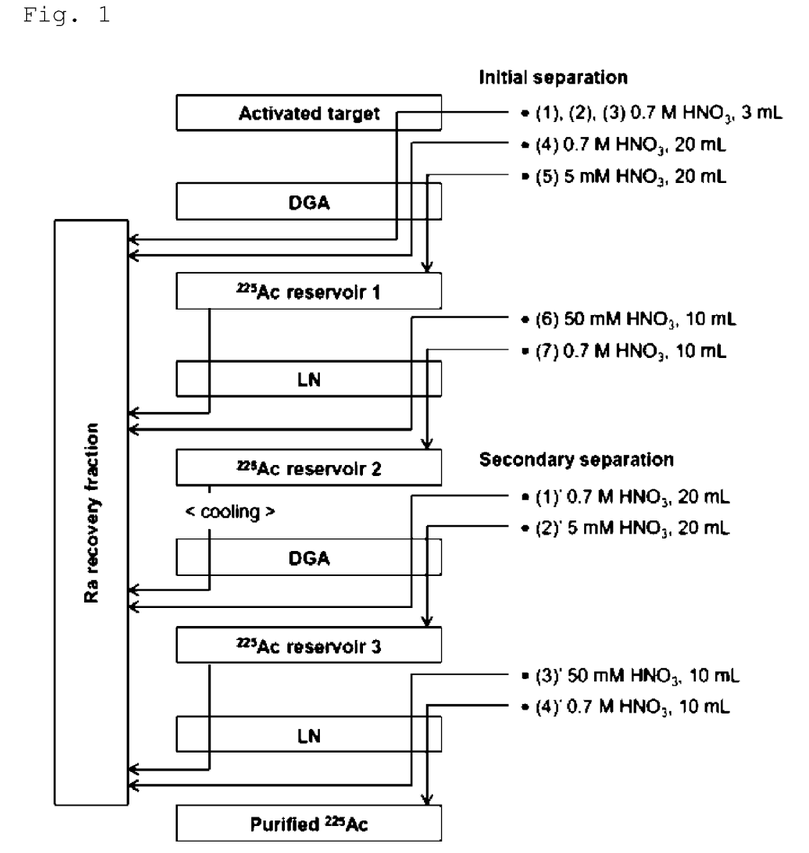
FIG. 1 is a flowchart of Example 2.

FIG. 1 shows the separation scheme implemented 3 to 4 days after the end of bombardment (EOB). The target bombarded by the cyclotron was dissolved in 3 mL of 0.7 M $HNO_3$, and the resulting solution was run through a DGA cartridge (N,N,N',N'-tetra-n-octyldiglycolamide, 1 mL, produced by Eichrom Technologies Inc.) at a rate of 0.8 mL/minute or less to capture $^{225}$Ac in the cartridge. In order to increase the recovery of Ac/Ra remaining in the target container, another 3 mL of 0.7 M $HNO_3$ was added to the target container twice, and each of the wash fractions was run through the DGA cartridge to capture $^{225}$Ac in the cartridge.

This DGA cartridge was washed with 20 mL of 0.7 M $HNO_3$ to wash away $^{226}$Ra remaining in the DGA cartridge. Next, 5 mM $HNO_3$ (20 mL) was run through the DGA at a rate of 0.8 mL/minute or less to elute $^{225}$Ac, and this fraction recovered in a vial. The crude $^{225}$Ac fraction was run through an Ln cartridge (di(2-ethylhexyl) orthophosphoric acid, 2 mL, produced by Eichrom Technologies Inc.), and the cartridge was washed with 10 mL of 50 mM $HNO_3$ to remove trace amounts of $^{226}$Ra mixed therein, followed by thorough purging. All of the fractions of the wash liquid were recovered as the Ra recovery fraction to be re-processed for the next use. Finally, 0.7 M HNO$_3$ (10 mL) was run through the Ln cartridge to elute $^{225}$Ac, and this fraction was recovered in another vial.

uncertainties are not included in the aforementioned assumptions; however, the aforementioned corrected cross-sections agreed well with the values calculated by ALICE code and TENDL code and actual observed values reported in previous studies.

TABLE 3

| Experiment | #1 | #2 | #3 |
|---|---|---|---|
| Beam conditions (Ep = 15.6 MeV) | 20 µA × 3 h | 20 µA × 5 h | 20 µA × 5 h |
| Ra deposition | | | |
| $^{226}$Ra, initial electrolyte | 14.5 MBq (391 µCi) | 36.4 MBq (984 µCi) | 38.8 MBq (1.05 mCi) |
| $^{226}$Ra deposited | 13.5 MBq (366 µCi) | 35.4 MBq (956 µCi) | 37.5 MBq (1.01 mCi) |
| Deposition rate (%) | 94 | 97 | 97 |
| Nuclides of interest* in the initially purified sample (kBq, decay corrected to EOB) | | | |
| $^{225}$Ac (150 keV, 0.6%) | 522 | 2.23 × 10$^3$ | 2.43 × 10$^3$ |
| $^{226}$Ac (230 keV, 26.9%) | 111 | 451 | 488 |
| $^{226}$Ra (186 keV, 3.64%) | Not detected | Not detected | Not detected |
| $^{214}$Pb (352 keV, 35.6%) | Not detected | Not detected | Not detected |
| $^{214}$Bi (609 keV, 45.5%) | 5.2 | 13.5 | 33.3 |
| $^{135}$La (481 keV, 1.52%) | 84.5 | 333 | 344 |
| $^{140}$La (487 keV, 43.9%) | 0.0571 | 0.165 | 0.231 |

*Nuclear data presented in parenthesis obtained from National Nuclear Data Center, NuDat 2.8 website https://www.nndc.bnl.gov/nudat2/chartNuc.jspAccessed Sep. 24, 2020 were used for quantification. The quantification was done by a 4096-channel calibrated HPGe well detector, with an uncertainty and a detection limit of 9% and 3.7 Bq, respectively (at the highest sensitivity, $^{225}$Ac: 1.2 × 10$^{-3}$%).

Table 3 shows the results of production (three runs) performed in this example. In Table 3, #1 indicates the results obtained when T1 was set to 5 days and T2 was set to 14 days, #2 indicates the results obtained when T1 was set to 4 days and T2 was set to 21 days, and #3 indicates the results obtained when T1 was set to 4 days and T2 was set to 28 days.

Figure 2:
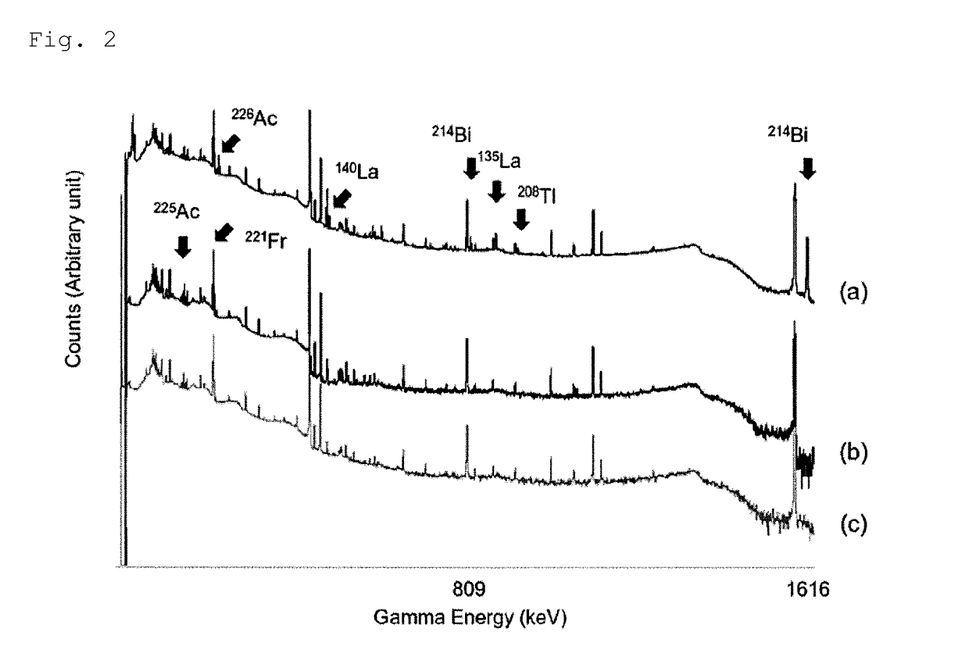

The $^{226}$Ra target prepared by electrodeposition on a cathode surface can be deemed to be a thin target of 1.0 to 1.5 mg/cm$^2$. The 226Ra (p, 2n)$^{225}$Ac cross-section (σ) was estimated to be 353 mb at 15.6 MeV. Related studies on such a nuclear reaction reported values of about 710 mb at 16.8 MeV (Apostolidis C, Molinet R, McGinley J, Abbas K, Mollenbeck J, Morgenstern A. Cyclotron production of Ac-225 for targeted alpha therapy. Appl Radiat Isot 2005; 62:383-387), 600+mb at 16.0 MeV (calculation by ALICE code, Apostolidis C, Molinet R, McGinley J, Abbas K, Mollenbeck J, Morgenstern A. Cyclotron production of Ac-225 for targeted alpha therapy. Appl Radiat Isot 2005; 62:383-387), and 522 mb at 16.0 MeV (calculated by TENDL-2019, TALYS-based evaluated nuclear data library (TENDL-2019) website https://tendl.web.psi.ch/tendl_2019/proton_html/Ra/ProtonRa226 xs.html Accessed Sep. 4, 2020), and these reported values are far higher. However, as described above, about ⅔ of the area of the target used here was covered with $^{226}$Ra due to unevenness on the surface, and thus the aforementioned σ can be multiplied by, for example, 1.56 (=1/0.64). Eventually, the values obtained as corrected estimated cross-sections of $^{226}$Ra (p, 2n)$^{225}$Ac and $^{226}$Ra (p, n)$^{226}$Ac were, respectively, 552 mb and 14 mb (reference: 34 mb for the (p, n) channel at 16 MeV, TALYS-based evaluated nuclear data library (TENDL-2019) website https://tendl.web.psi.ch/tendl_2019/proton_html/Ra/ProtonRa226 xs.html Accessed Sep. 4, 2020). Although the Ac separation efficiency, the beam profile, and the Ba/Ra ratio can give some errors in the evaluation, quantitative corrections for these possible factors could not be applied to the present example. Thus, these Separation As illustrated in FIG. 2(a), presence of $^{226}$Ac and other foreign radionuclides was detected from the $^{225}$Ac sample after the initial separation. $^{226}$Ac is, like $^{226}$Ra, a 4n+2-series radionuclide that generates many descendant nuclides during the cooling period. Thus, the 4n+2-series impurities emitted during the course of decay of $^{226}$Ac could be removed by repeated separation performed as secondary purification, and thus high-quality $^{225}$Ac was generated. Under the aforementioned irradiation conditions, $^{224}$Ac (EC: 91%, α: 9%, T$_{1/2}$=2.8 hours) should have occurred as a byproduct via the $^{226}$Ra(p, 3n) channel (E$_{TH}$=13.6 MeV); however, the half-life of $^{224}$Ac is very short, and $^{224}$Ac could not be detected upon completion of the separation 4 days from EOB. However, prominent distributions were detected for two $^{224}$Ac descendant nuclides associated with gamma emission in the 4n series, namely, $^{212}$Bi (T$_{1/2}$=61 minutes, 727 keV, 6.7%) and $^{208}$Tl (T$_{1/2}$=3.1 minutes, 2615 keV, 99%), in both the wash fractions and separated products, and these were also detected in trace amounts in the purified $^{225}$Ac sample. This was the evidence of generation of $^{224}$Ac. The presence of $^{212}$Bi and $^{208}$Tl in the $^{225}$Ac fraction is reasonable since Bi and Ac show partial similarity under the separation conditions employed here. Meanwhile, the parent nuclide of $^{212}$Bi, that is, $^{212}$Pb (T$_{1/2}$=10.6 hours, 239 keV, 44%), was not detected in the purified $^{225}$Ac sample. All 4n-series nuclides ($^{224}$Ac to $^{216}$Po (excluding $^{224}$Ra)) that can be parent nuclides of $^{212}$Pb have half-lives shorter than $^{212}$Pb, and thus $^{224}$Ra was removed together with $^{226}$Ra. Thus, the byproduct radionuclides that should be taken care of in the separation process are considered to be mainly those of the 4n+2 series.

Figure 3:
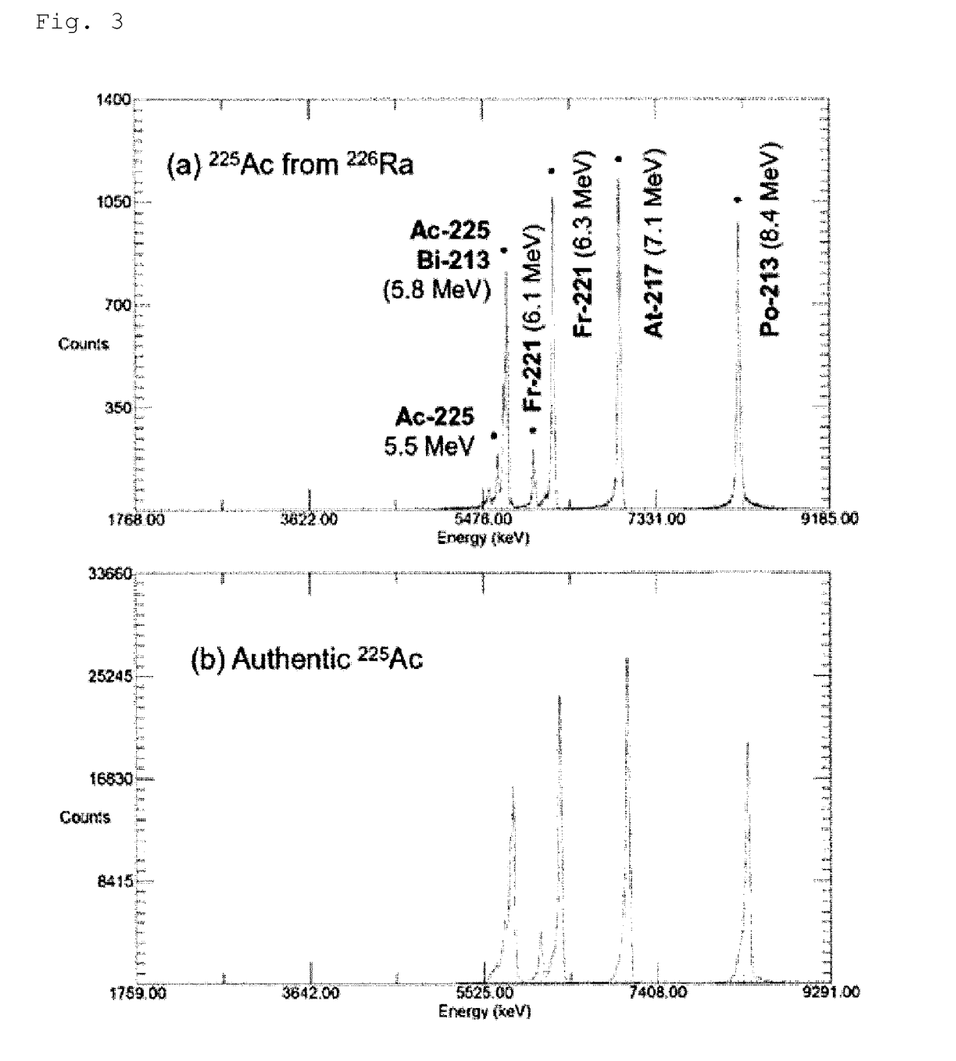
FIG. 3 shows alpha spectra of $^{225}$Ac products obtained by measuring aliquots of $^{225}$Ac (0.37 to 1.85 kBq), which were dried on Al disks, without coating. (a) in FIG. 3 is an alpha spectrum of the purified $^{225}$Ac product 19 days after EOB in Example 2, and (b) in FIG. 3 is a alpha spectrum of a commercially available reference $^{225}$Ac.

Other byproducts that needed care were $^{135}$La (EC, T$_{1/2}$=19.5 hours) and $^{140}$La (β, T$_{1/2}$=1.68 days). The former is considered to be a produced as a byproduct via $^{135}$Ba(p, n) channel from a natural Ba carrier contained in a legacy Ra source. However, the half-life of $^{135}$La is far shorter than the half-life of $^{225}$Ac, and thus it is considered that the $^{135}$La-to-$^{225}$Ac ratio will gradually decrease during an appropriate cooling period without having to remove contaminant Ba from extracted Ra. Meanwhile, since the heaviest stable isotope of Ba is $^{138}$Ba, $^{140}$La is considered to have an atomic mass too large for it to be generated by proton irradiation. In other words, this suggests that $^{140}$La could be generated by nuclear fission of $^{226}$Ra when $^{226}$Ra was irradiated. Furthermore, a parent nuclide of $^{140}$La, $^{140}$Ba (β, $T_{1/2}$=12.6 days), could also be generated as another nuclear fission product. Since $^{140}$Ba has a longer half-life than $^{225}$Ac, the decrease in the ratio of $^{140}$Ba generated as a result of decay and $^{140}$La, which is a daughter nuclide thereof, to $^{225}$Ac cannot be expected. To address this, the initial separation was carried out within several days after the end of cyclotron bombardment to remove $^{140}$Ba, which has similar chemical behavior to $^{226}$Ra, along with $^{226}$Ra from the $^{225}$Ac fraction by initial separation so that only $^{140}$La was in the $^{225}$Ac fraction. Actually, $^{140}$La, which was detected in trace amounts in the $^{225}$Ac fraction, exhibited decay in a half-life of 1.67±0.10 days, which agreed well with the nominal half-life of 1.68 days, and had decayed to an undetectable level in the gamma spectrum in 2 to 3 weeks of subsequent cooling. In other words, the initial purification could decrease the $^{140}$La-to-$^{225}$Ac ratio. For example, when the aforementioned sample was cooled for 19 to 20 days after EOB or for two weeks after the end of separation, a spectrum similar to that of $^{225}$Ac produced by a different production method, $^{229}$Th/$^{225}$Ac generator (FIG. 2(b) and FIG. 2(c)), was obtained. As shown in FIG. 3, the alpha spectrum of the $^{225}$Ac products here also had a similar profile to the aforementioned reference substance, and, in particular, detection of $^{226}$Ra (Eα=4.78 MeV, 94%) and $^{210}$Po (Eα=5.30 MeV, 100%) was not found. Thus, it was concluded that double separation with an appropriate cooling period produces purified $^{225}$Ac having quality comparable to $^{225}$Ac produced by a $^{229}$Th/$^{225}$Ac generator.

Example 3

(1-1. Complex Formation Step)

Chelating agents represented by formulae (L1 and L2) were used. The DOTA-DECO represented by formula (L1) below was synthesized by the method described in Wang H et al. Selective in vivo metabolic cell-labeling-mediated cancer targeting. Nat Chem Biol. 13(4): 415-424. (2017). The DOTAGA-DECO represented by formula (L2) below was synthesized by the method described in Bernhard et al. DOTAGA-Anhydride: A Valuable Building Block for the Preparation of DOTA-Like Chelating Agents, Chem. Eur. J. 18(25): 7834-7841. (2012).

DOTA-DBCO (L1)

DOTAGA-DBCO (L2)

Each one of the chelating agents and the $^{225}$Ac solution obtained by the method described in Example 1 were reacted in a sodium acetate buffer (pH 6.0) at 70° C. for 90 minutes to obtain liquids ($^{225}$Ac complex liquids) that contained the chelating agents that had formed complexes with $^{225}$Ac.

(1-2. Antibody Modification Step)

Separately, a peptide was produced by the method described in International Publication No. 2017/217347 to obtain a peptide represented by formula (P3) below containing 17 amino acid residues. The amino acid sequence of this peptide was the same as the sequence No. (2) with a lysine residue in Xaa2, and the side chain terminal amino group of the lysine residue is modified with the structure represented by $R_1$. Moreover, two cysteine residues form a disulfide bond with each other, and the N terminal of the peptide is bonded to ethylazide, which is an azide group-containing atomic group serving as a reactive atomic group, via a linker structure that has diglycol acid and eight PEGs.

(P3)

[In formula (P3), Gly represents glycine, Pro represents proline, Asp represents aspartic acid, Cys represents cysteine, Ala represents alanine, Tyr represents tyrosine, His represents histidine, Glu represents glutamic acid, Leu represents leucine, Val represents valine, Trp represents tryptophan, and Phe represents phenylalanine.]

A liquid mixture prepared by mixing the peptide represented by formula (P3) above and a human IgG antibody (trastuzumab produced by F. Hoffmann-La Roche Ltd.) with a sodium acetate buffer (pH 6) was reacted at room temperature for 30 minutes to obtain a solution that contains a peptide-modified antibody. This peptide-modified antibody had an Fc region that was site-specifically modified with the aforementioned peptide.

(2. Labeling Step)

1-2. To a solution obtained in the antibody modification step and containing the peptide-modified antibody, each one of the $^{225}$Ac complex liquids obtained in the 1-1. Complex formation step was added as crude, and the click reaction was performed at 37° C. for 120 minutes to obtain conjugates. Furthermore, the obtained solutions of the conjugates were purified by using an ultrafiltration filter (model UFC505096 produced by Merck Co., Inc.).

The radiochemical purity and radiochemical yield of the conjugates were measured as follows.

A thin layer chromatography (model: SGI0001 produced by Agilent Technologies, Inc., developing solvent: liquid mixture (volume ratio=1:1) of acetonitrile and 0.1 mmol/L of an EDTA solution (pH 5.0)) was measured with a scanner-type image analyzer (MODEL Typhoon FLA7000 produced by GE Healthcare), and the percentage of the peak radioactivity (counts) detected near the origin with respect to the total radioactivity (counts) detected was assumed to be the radiochemical purity (%). Measurement was carried out with a gamma-particles spectrometer (MODEL GMX15P4 produced by ORTEC), and the percentage of the radioactivity (count) of the conjugate obtained after purification in the labeling step with respect to the total radioactivity (counts) applied during the complex formation step was assumed to be the radiochemical yield (%). The measurement results are shown in Table 5.

TABLE 5

| Chelating agent | Radioactivity of feed (kBq) | Radiochemical purity (%) | Radiochemical yield (%) |
| --- | --- | --- | --- |
| DOTA-DBCO | 259 | 92 | 32 |
| DOTAGA-DBCO | 267 | 99 | 30 |

The obtained conjugate was diluted with physiologic saline to obtain a medicine that contains, as an active ingredient, a conjugate between a chelating agent that has formed a complex with $^{225}$Ac, and trastuzumab.

Example 4

A commercially available Daptomycin (produced by Tokyo Chemical Industry Co., Ltd.) was dissolved in dimethylformamide, triethylamine and DOTABnSCN were added thereto, and the resulting mixture was reacted at 50° C. for 120 minutes. The obtained reaction liquid was separated and purified by reversed phase silica gel chromatography, and DOTA-Daptomycin (formula (L3) below) was obtained as a result.

DOTA-Daptomycin and 258 kBq of the $^{225}$Ac solution obtained by the method described in Example 1 were reacted in a liquid mixture of 0.5 mol/L of a tetramethylammonium acetate buffer (pH 7.8) and an aqueous ethanol solution under heating conditions of 70° C. and 1 hour, and a conjugate was obtained as a result.

DOTA-Daptomycin

The radiochemical purity of the obtained conjugate was measured by the following method. That is, by using a thin layer chromatography (iTLC-SG produced by Agilent Technologies, Inc., developing solvent: 0.1 mol/L EDTA solution (pH 5.0)), the percentage of the radioactivity count of the chelating agent that had formed a complex with $^{225}$Ac with respect to the total $^{225}$Ac radioactivity count including unreacted $^{225}$Ac was assumed to be the radiochemical purity (%). As a result, the radiochemical purity was 99.9% or higher.

The obtained conjugate was diluted with physiologic saline to obtain a medicine that contained, as an active ingredient, a conjugate between a chelating agent that had formed a complex with $^{225}$Ac, and Daptomycin.

The invention claimed is:

1. A method for producing an $^{225}$Ac solution, the method comprising:
    a step (I) of irradiating a $^{226}$Ra target with at least one type of particles selected from protons, deuterons, and photons to generate two or more actinium radioisotopes (Ac) including at least $^{225}$Ac;
    a step (II) of dissolving the $^{226}$Ra target after the step (I) to obtain a Ra—Ac solution (1) that contains $^{226}$Ra and Ac;
    a step (III) of separating $^{226}$Ra and Ac originating from the $^{226}$Ra target and contained in the Ra—Ac solution (1) to obtain an Ac solution (2) that has a higher Ac concentration than the Ra—Ac solution (1);
    a step (IV) of allowing $^{224}$Ac and $^{226}$Ac in the Ac solution (2) to decay to obtain a Ra—Ac solution (3) containing radium isotopes (Ra) resulting from decay; and
    a step (V) of separating Ra and Ac contained in the Ra—Ac solution (3) to obtain an Ac solution (4) that has a higher $^{225}$Ac concentration than the Ra—Ac solution (3),
    when a time from completion of the step (I) to start of the step (III) is represented by T1, and
    a time from completion of the step (III) to start of the step (V) is represented by T2,
    T1 and T2 satisfy a relationship of T2>T1,
    wherein a ratio $^{140}$La content/$^{225}$Ac content of a $^{140}$La content to an $^{225}$Ac content in the Ac solution (4) is $1 \times 10^{-5}$ or less at seven days after completion of the step (V).

2. The method for producing an $^{225}$Ac solution according to claim 1, wherein the time T1 is shorter than seven days.

3. The method for producing an $^{225}$Ac solution according to claim 1, wherein, in the step (III) or (V), a solid-phase extraction agent that captures Ra is used or Ac is colloidized.

4. The method for producing an $^{225}$Ac solution according to claim 3, wherein the solid-phase extraction agent is at least one selected from a cation-exchange resin, a solid-phase extraction agent (a) containing a compound represented by the following formula (A), a solid-phase extraction agent (b) containing a compound represented by the following formula (B), and a solid-phase extraction agent (c) containing a compound represented by the following formula (C):

wherein, in formula (A), m and n each independently represent 0 or 1, and $R^1$ to $R^4$ each independently represent an alkyl group having 8 to 12 carbon atoms, (B)

wherein, in formula (B), $R^5$ and $R^6$ each independently represent an alkyl group having 8 carbon atoms or an alkoxy group having 8 carbon atoms, (C)

wherein, in formula (C), R8 to R9 each independently represent a hydrogen atom or an alkyl group having 1 to 6 carbon atoms.

5. The method for producing an $^{225}$Ac solution according to claim 1, wherein the Ac solution (4) is used for producing a medicine that contains, as an active ingredient, a conjugate between a chelating agent that has formed a complex with $^{225}$Ac, and a targeting agent.

* * * * *